US010335085B2

(12) United States Patent
Allen (10) Patent No.: US 10,335,085 B2
(45) Date of Patent: Jul. 2, 2019

(54) DEVICE AND METHOD FOR DETECTION OF PERIODIC LEG MOVEMENTS (71) Applicant: THE JOHNS HOPKINS UNIVERSITY, Baltimore, MD (US)

(72) Inventor: Richard P. Allen, Arnold, MD (US)

(73) Assignee: The Johns Hopkins University, Baltimore, MD (US)

( * ) Notice: Subject to any disclaimer, the term of this patent is extended or adjusted under 35 U.S.C. 154(b) by 353 days.

(21) Appl. No.: 15/119,405

(22) PCT Filed: Feb. 12, 2015

(86) PCT No.: PCT/US2015/015556
§ 371 (c)(1),
(2) Date: Aug. 17, 2016

(87) PCT Pub. No.: WO2015/123384
PCT Pub. Date: Aug. 20, 2015

(65) Prior Publication Data
US 2017/0049396 A1 Feb. 23, 2017

Related U.S. Application Data (60) Provisional application No. 61/940,623, filed on Feb. 17, 2014.

(51) Int. Cl.
*A61B 5/00* (2006.01)
*A61B 5/11* (2006.01)
(52) U.S. Cl.
CPC .......... *A61B 5/6828* (2013.01); *A61B 5/0022* (2013.01); *A61B 5/1107* (2013.01);
(Continued)

(58) Field of Classification Search
CPC ......... A61B 5/11; A61B 5/112; A61B 5/1114; A61B 5/1123; A61B 5/0022;
(Continued)

(56) References Cited

U.S. PATENT DOCUMENTS 5,963,891 A 10/1999 Walker et al.
9,999,378 B2 * 6/2018 Ronchi ................ A61B 5/4595
(Continued)

OTHER PUBLICATIONS

Extended European Search Report dated Aug. 25, 2017 for EP application 15749160.6.
(Continued)

*Primary Examiner* — Max F Hindenburg
(74) *Attorney, Agent, or Firm* — Harrity & Harrity, LLP (57) ABSTRACT The present invention is directed to a computer application for monitoring and tracking leg and foot movements and positions and a device for facilitating the computer tracking of the leg and foot movements. The application uses an accelerometer, gyroscope or other movement detectors in available devices such as a phone, movement tracker, personal music device, tablet computing device, other similar device or a device specifically designed to detect movements and positions and to track the movement and changes in position of the patient's leg and foot. The device can be held onto the patient's leg using a band type device that is easy to use and comfortable during sleep or by incorporation into a comfortable wearable band. The application includes a user interface and a backend for use by physicians or other healthcare staff to review and diagnose the patient's leg and foot movement patterns.

22 Claims, 8 Drawing Sheets (52) U.S. Cl.
CPC .......... *A61B 5/1114* (2013.01); *A61B 5/1123* (2013.01); *A61B 5/4806* (2013.01); *A61B 5/4815* (2013.01); *A61B 5/4857* (2013.01); *A61B 5/6829* (2013.01); *A61B 5/6831* (2013.01); *A61B 5/6898* (2013.01); *A61B 5/742* (2013.01)

(58) Field of Classification Search
CPC ... A61B 5/1107; A61B 5/4806; A61B 5/6828; A61B 5/6829
See application file for complete search history.

(56) References Cited

U.S. PATENT DOCUMENTS

| | | |
|---|---|---|
| 2008/0204225 A1 | 8/2008 | Kitchen |
| 2009/0040041 A1 | 2/2009 | Janetis et al. |
| 2010/0035688 A1 | 2/2010 | Picunko |
| 2010/0298742 A1 | 11/2010 | Perlman et al. |
| 2012/0130280 A1 | 5/2012 | Lee |
| 2012/0232431 A1 | 9/2012 | Hudson |

OTHER PUBLICATIONS

King, et al., "The validation of a new actigraphy system for the measurement of periodic leg movements in sleep" 'Sleep Medicine (2005) vol. 6, No. 6, pp. 507-513.
Rias, et al., "Detecting periodic limb movements with off-the-shelf accelerometers: a feasibility study" Studies in Health Technology and Informatics, (2013) pp. 152-156.

\* cited by examiner

DEVICE AND METHOD FOR DETECTION OF PERIODIC LEG MOVEMENTS

CROSS-REFERENCE TO RELATED APPLICATIONS

This application is a 35 U.S.C. § 371 U.S. national entry of International Application PCT/US2015/015556, having an international filing date of Feb. 12, 2015, which claims the benefit of U.S. Provisional Application No. 61/940,623, filed Feb. 17, 2014, the content of each of the aforementioned applications is herein incorporated by reference in their entirety.

FIELD OF THE INVENTION

The present invention relates generally to a medical computer application. More particularly, the present invention relates to a device and method for detection of periodic leg and foot movements that are the motor sign of the restless leg syndrome and also relate to other health and sleep conditions.

BACKGROUND OF THE INVENTION

Many people experience involuntary leg and foot movements, especially during sleep and sometimes during lying down resting while awake. These movements can be tied to sleep disruption that can shorten the duration and reduce the quality of a person's sleep. The characteristics of involuntary leg and foot movements include periodicity (periodic leg movements (PLM)), inter-movement intervals, durations, frequency (at a rate of approximately 5-300/hr), intensity, flexor movement patterns and circadian pattern. They occur when the leg is mostly horizontal with the person either lying down or sitting with legs stretched out. Thus, in addition to detection of movement, detection of horizontal vs. vertical, supine vs. lateral or prone leg position and foot relative to leg positioning are relevant for evaluating these movements. These leg and foot movements can be caused by a number of different factors, either alone or in combination. Such factors include, but are not limited to spinal cord excitability, autonomic arousals, dopaminergic compromise, hypoxic pathway activation, iron deficiency, and genetics, namely a BDBT9 allele.

When these leg and foot movements occur during sleep, they can be clinically significant. They occur with disturbances in sleep even waking up the sufferer. Different patterns of leg and foot movements can indicate different possible disease states such as restless leg syndrome (Willis Ekbom Disease), sleep disordered breathing, iron deficiency, REM behavior disorder, narcolepsy, significant increases in blood pressure, and cardiovascular disease. Leg and foot movements can be an indicator of a worsening condition when present with other serious disorders, such as iron deficiency/anemia, renal disease, and cardiovascular disease.

It would therefore be advantageous to provide an affordable, easily-used device and method for detecting periodic leg movements and allowing accurate measurement of patterns of leg and foot movements in a large number of people in order to quantify whether the patient has a disease state associated with the leg movements.

SUMMARY OF THE INVENTION

The foregoing needs are met by the present invention which provides a method for tracking leg movements in a patient including positioning an accelerometer or other leg and foot movement detector device on a leg of the patient and activating the detector device or devices to collect data regarding movement and/or position of the leg and foot using a patient-based computer application. The method includes collecting the relevant data regarding movement and position of the leg and foot and transmitting the relevant data regarding movement and position of the leg and foot to a provider-based computer device. Additionally, the method includes processing the relevant data regarding movement and position of the leg and foot. The relevant data is that available from the device and is needed for identification of the periodic leg movements.

In accordance with an aspect of the present invention, the method includes generating graphical and numeric output representing the movement and position of the leg and foot. The method can include repeating the steps of the method for a predetermined period of time, and generating graphical and numeric output representing the movement and position of the leg and foot over the predetermined period of time. Additionally, the method includes prompting the user to activate the patient-based computer application before the patient initiates a sleep cycle and prompting the user to terminate the patient-based computer application when the patient wakes up from a sleep cycle. The method can also include fixing the patient-based computer application on a non-transitory computer readable medium. An accelerometer fixed in a device selected from a group consisting of a smartphone, a phablet, a tablet, a personal music device, or a fitness tracker can be used. Other measurements of leg or foot movements or position in other fixed devices can also be used. Further, the method includes positioning the device in a mount on a strap or as part of a wearable band that can be secured to the leg of the patient. The method also includes storing data related to movement and position of the leg and foot as it is collected either in the device with the movement and position sensors or by transmission to a separate device where it may be held, partially analyzed and then transmitted to a database for more complete analysis. The more complete analysis with graphical and numerical display could be sent back to the person's devices and also provided for other appropriate computer medium display and record.

BRIEF DESCRIPTION OF THE DRAWINGS

The accompanying drawings provide visual representations, which will be used to more fully describe the representative embodiments disclosed herein and can be used by those skilled in the art to better understand them and their inherent advantages. In these drawings, like reference numerals identify corresponding elements and.

DETAILED DESCRIPTION

The presently disclosed subject matter now will be described more fully hereinafter with reference to the accompanying Drawings, in which some, but not all embodiments of the inventions are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains, having the benefit of the teachings presented in the foregoing descriptions and the associated Drawings. Therefore, it is to be understood that the presently disclosed subject matter is not to be limited to the specific embodiments disclosed and that modifications and other embodiments are intended to be included within the scope of the appended claims.

The present invention is directed to a computer application for monitoring and tracking leg and foot movements and position and a device for facilitating the computer tracking of the leg and foot movements and position. The application uses an accelerometer in a device such as a phone, movement tracker, personal music device, tablet computing device, phablet, or other similar device to track the movement and position of the person's leg and foot. The device can be held onto the patient's leg using a band type device or by incorporation in a wearable band that is easy to use and comfortable during sleep. The application includes a user interface and a backend for use by physicians or other healthcare staff to review and diagnose the patient's leg movement patterns.

Figure 1:
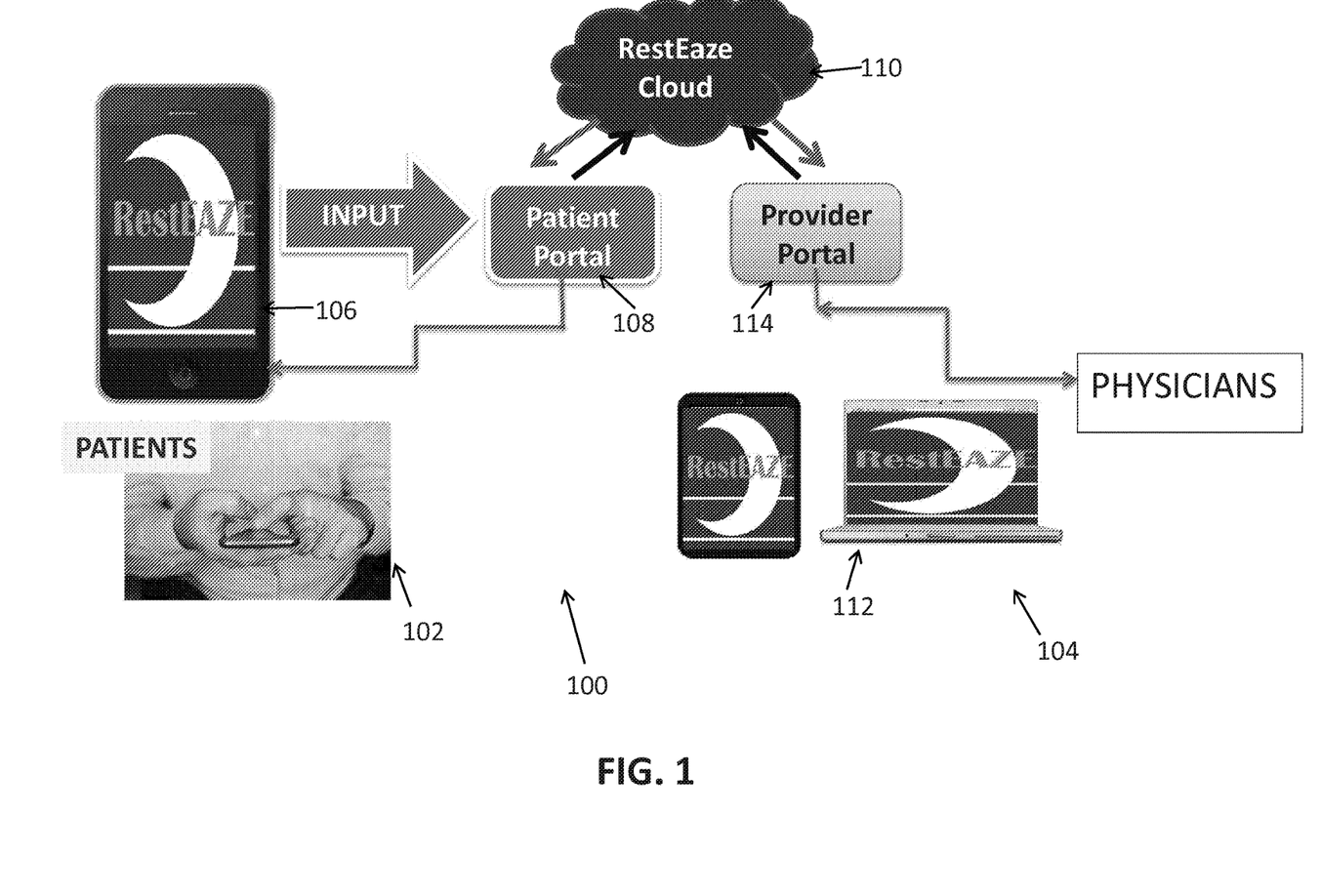
FIG. 1 illustrates a schematic view of a computer application system according to an embodiment of the present invention.

FIG. 1 illustrates a schematic view of a computer application system according to an embodiment of the present invention. As illustrated in FIG. 1 the computer application system 100 is divided into a patient application system 102 and a provider application system 104. The patient application system 102 includes an application for installation on a device with accelerometer 106, such as a smart phone, tablet, phablet, personal music device, movement tracker, or other similar device containing an accelerometer. The computer application is activated by the patient and used to collect data. The steps taken by the patient to activate data collection will be described in more detail below with respect to FIGS. 2-5. The data and other patient information collected by patient use of the application is uploaded through the patient portal 108 to the application system cloud 110. Once patient data is uploaded to the application system cloud 110, a physician or health care provider can access the data using the provider application system 104. The provider can use a corresponding computer application on a computing device 112 such as a PC, smart phone, tablet, phablet, personal music device, movement tracker, or other similar device. The provider accesses the information through the provider portal 114.

Figure 2:
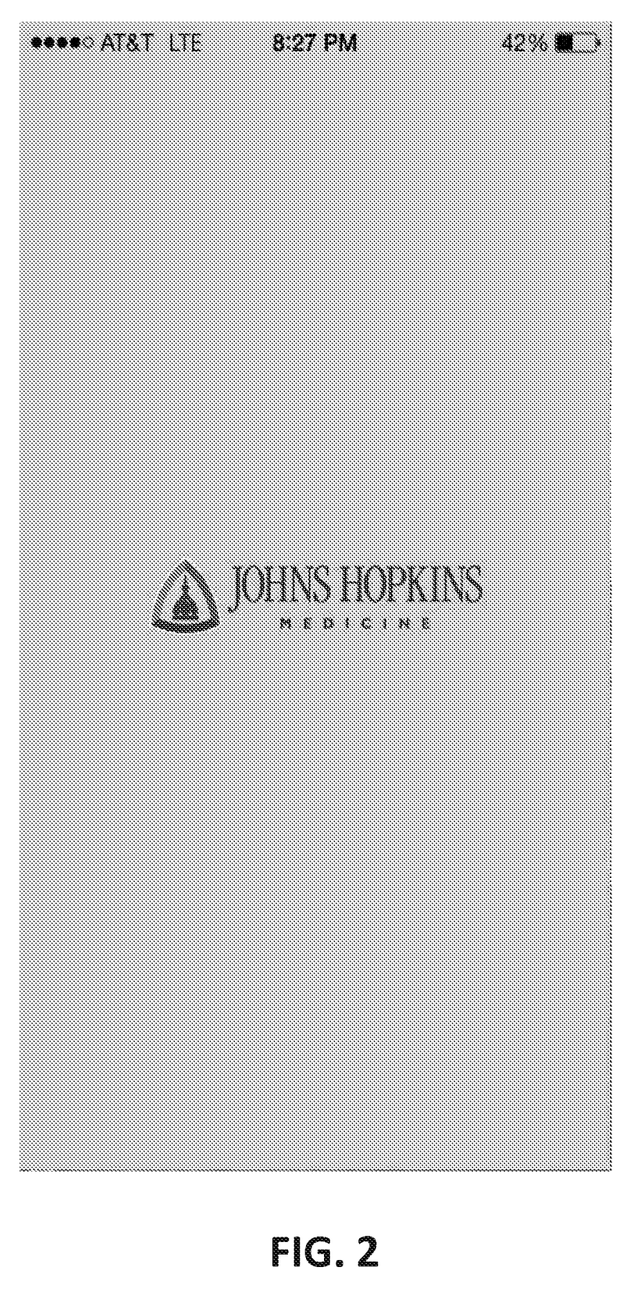
FIGS. 2-5 illustrate exemplary screen shots of the patient application system as displayed on an exemplary smartphone device for guiding the patient through data collection, according to an embodiment of the present application.

FIGS. 2-5 illustrate exemplary screen shots of the patient application system as displayed on an exemplary smartphone device for guiding the patient through data collection, according to an embodiment of the present application. More particularly, FIG. 2 illustrates a loading screen for the application, according to an embodiment of the invention. The loading screen is displayed while the application is initializing. The loading screen can display any relevant information such as the name of the application, the developers, sponsoring hospitals or companies, or any other information suitable for the user. While a screen shot of an exemplary loading screen in illustrated in FIG. 2, the application need not display anything during loading, or the loading screen can take any other suitable form known to or conceivable by one of skill in the art.

Figure 3:
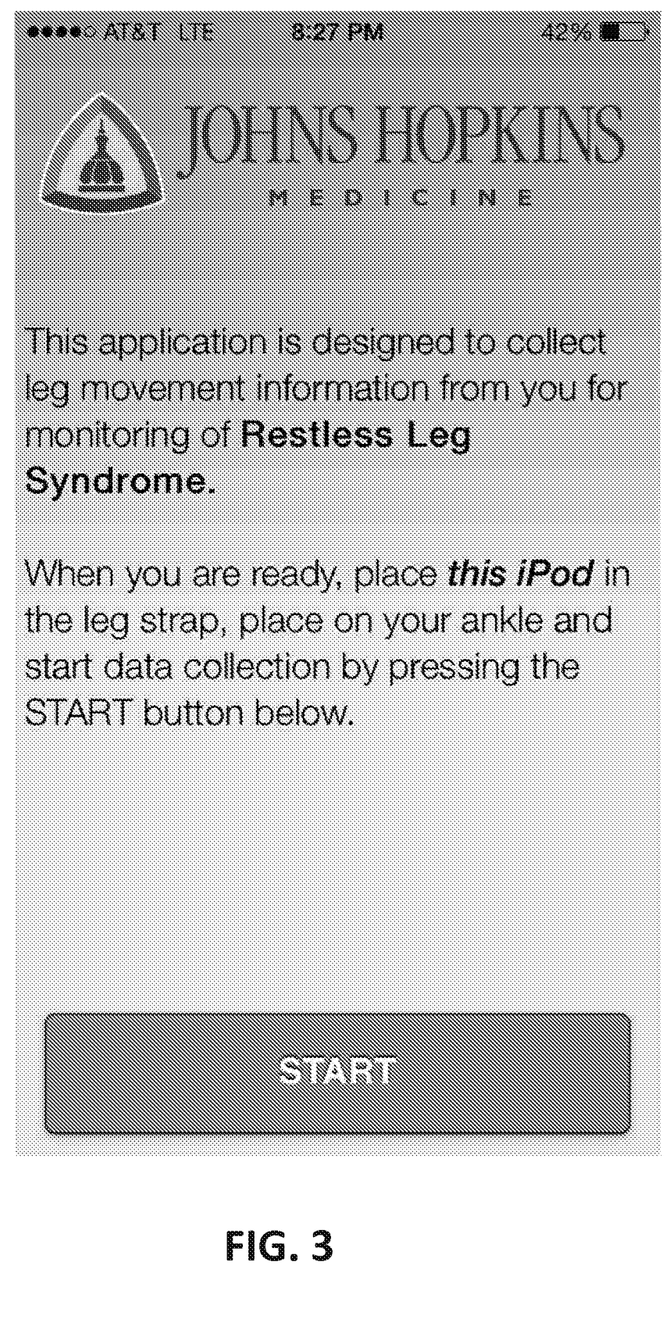

FIG. 3 illustrates a start screen for triggering data collection of a patient's leg and foot movements, according to an embodiment of the present invention. The start screen provides instructions to the patient for collecting the leg and foot movement data. For example, the exemplary start screen illustrated in FIG. 3, states "This application is designed to collect leg movement information from you for monitoring of Restless Leg Syndrome. When you are ready, place this iPod in the leg strap, place on your ankle and start data collection by pressing the start button below." The language could be varied from user to user depending on what type of disease state or leg and foot movement is being monitored and what type of device they are using for data collection. Indeed, any suitable instructions to prompt data collection by the patient known to or conceivable by one of skill in the art could be used.

Figure 4:
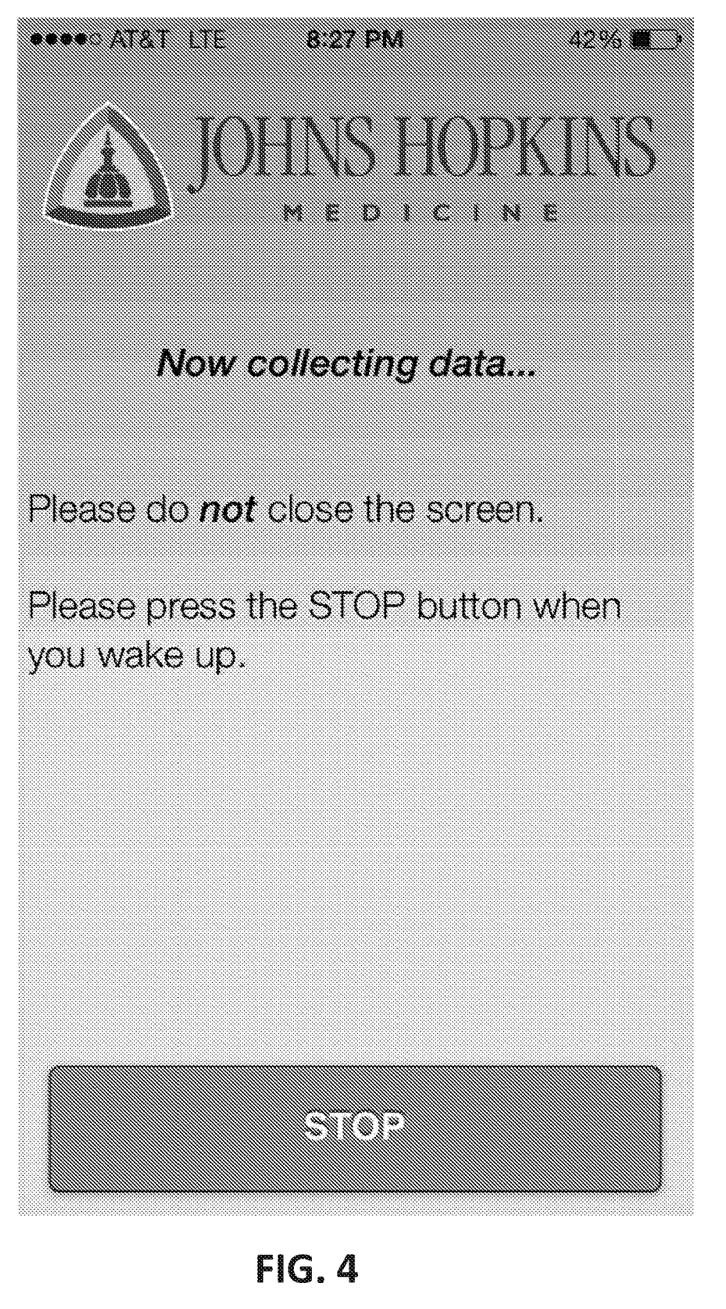

FIG. 4 illustrates a working screen, displayed during data collection, according to an embodiment of the invention. The working screen provides instructions for the patient to follow while the application is in use and data is being collected. For instance, in FIG. 4, the exemplary screen states that the application is "Now collecting data . . . " Further, the application advises the patient, "Please do not close the screen." Additionally, the exemplary working screen provides instructions for stopping the application after the patient wakes up. The screen states, "Please press the STOP button when you wake up." A stop button is featured at the bottom of the screen to allow the patient to end the application when he or she is awake. Any suitable instructions to prompt the user during data collection and for ending data collection known to or conceivable by one of skill in the art could also be used.

Figure 5:
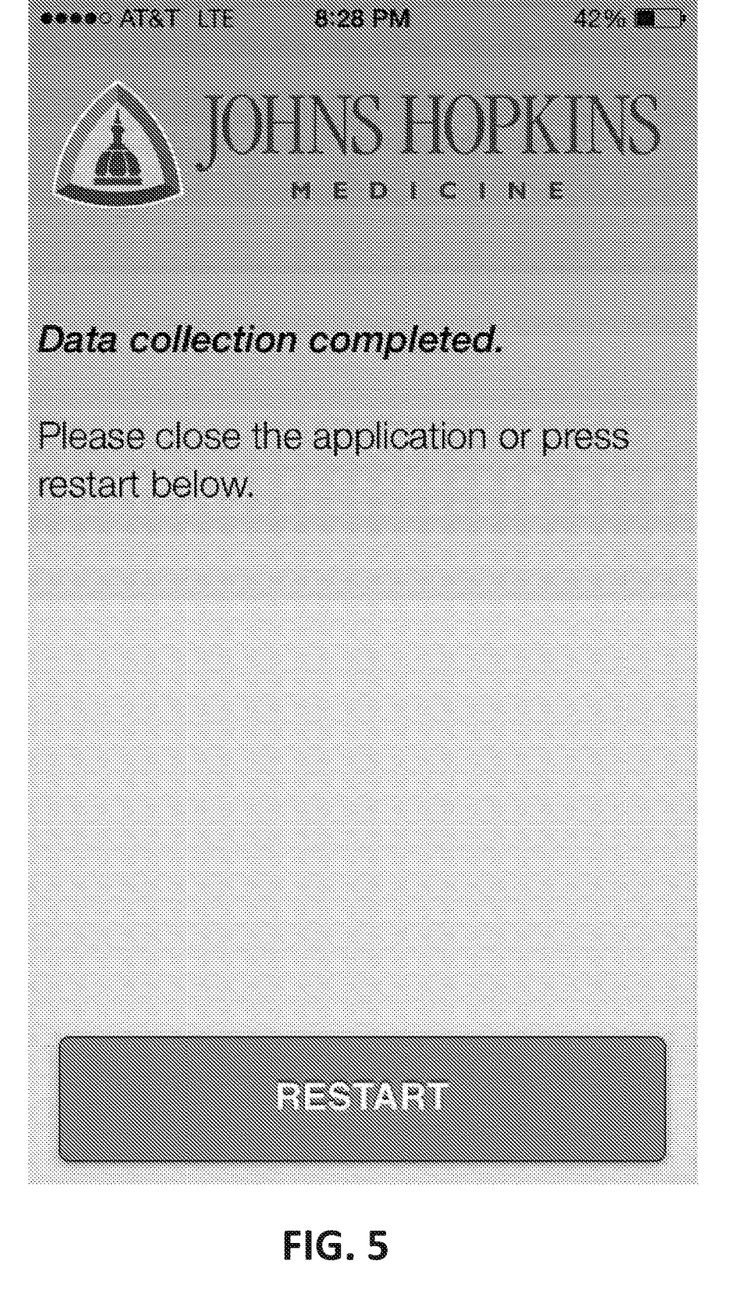

FIG. 5 illustrates an exemplary closing page, displayed after the conclusion of data collection, according to an embodiment of the invention. The closing screen alerts the patient that data collection is completed. The closing screen informs the patient that the application can be closed or restarted using the "restart" button positioned at the bottom of the screen. Any suitable instructions to prompt the user to close the application or restart the application known to or conceivable by one of skill in the art can be used.

In use, the accelerometer or other leg and foot activity measuring device tracks the leg movement of the patient. Leg and foot position may also be determined by a gyroscope or another feature of the device. A graphic output showing patterns of leg and foot movement over a night or series of nights can be generated for observation by the patient and use by the health care provider or physician. Graphic and numeric outputs of overall sleep quality, leg positions, rate of leg and foot movement, periodicity of leg movement, intensity of leg and foot movement, and circadian rhythm can also be provided. These graphic and numerical outputs can be used to indicate need for medical consult. The computer application can also include database capabilities for data storage and comparison. Data can also be studied in order to determine correlations and provide for more accurate diagnosis. Another feature includes allowing for cloud-based, detailed analysis with medical consult and recommendations. The computer application also transmits data to the healthcare provider such that feedback and diagnosis can be provided to the patient either in-office or using a telemedicine framework.

Figure 6:
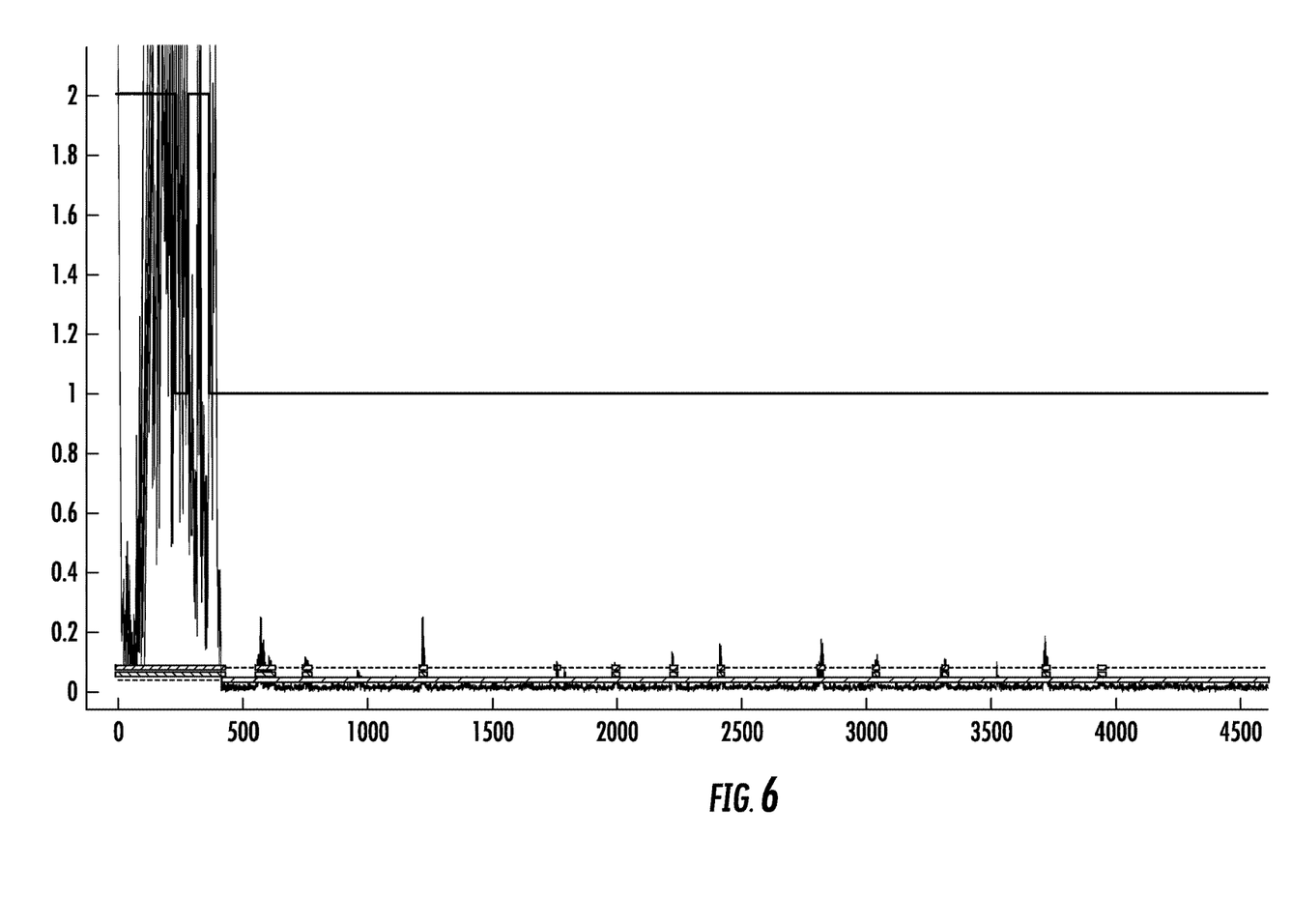
FIG. 6 illustrates a graphical view of an exemplary lab validation related to the recorded data of a leg movement study subject.
Figure 7:
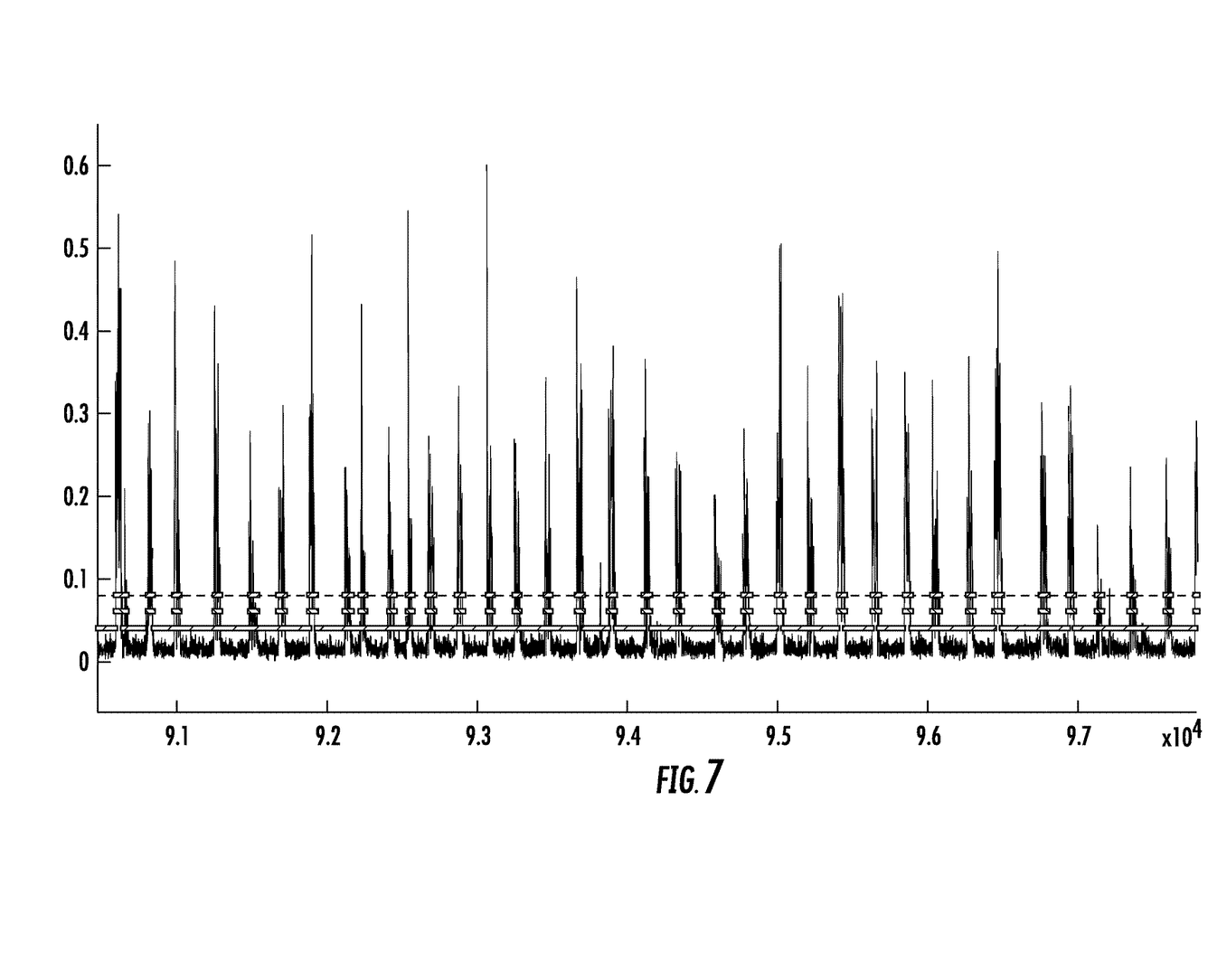
FIG. 7 illustrates a graphical view of an exemplary detailed graphical output according to an embodiment of the present invention.

FIG. 6 illustrates a graphical view of an exemplary lab trial related to the recording of leg position change at onset of sleep based on the gyroscope in one embodiment of the present invention. FIG. 6 illustrates 7.7 minutes of recording. The top horizontal bar represents leg position change to supine at onset of sleep period. The lower horizontal bars indicate movements that meet the criteria for periodic leg/foot movements. FIG. 7 illustrates a graphical view of an exemplary detailed graphical output according to an embodiment of the present invention. FIG. 7 illustrates a 13.3 minute recording. The middle non-dashed horizontal bar indicates movements that meet criteria for periodic leg/foot movements from a supine leg position with adequate activity, duration and periodicity for time.

Figure 8:
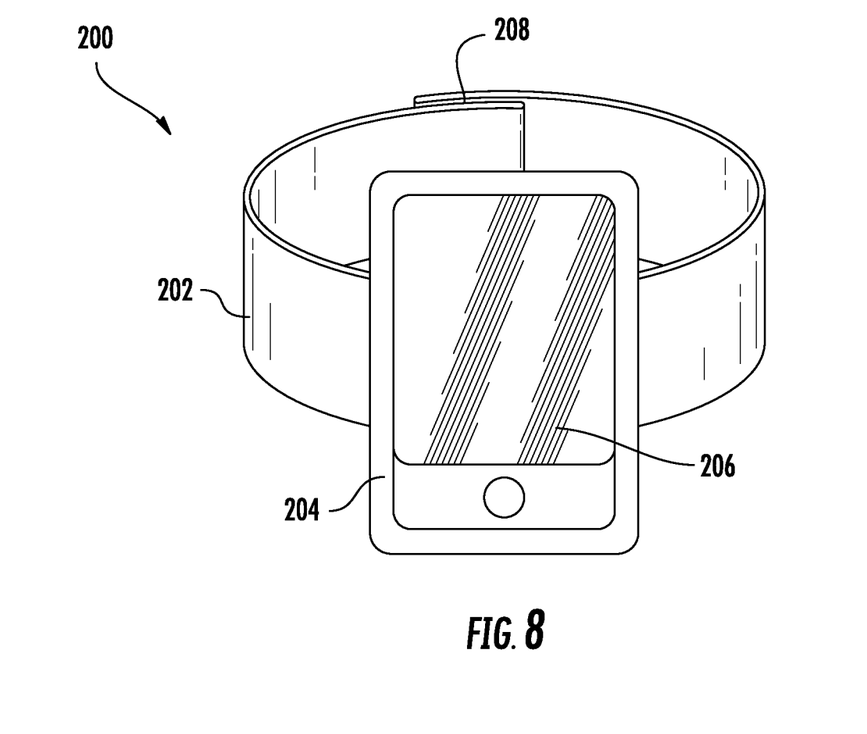
FIG. 8 illustrates a perspective view of a band type device for securing the accelerometer based device to the patient during data collection, according to an embodiment of the present invention.

FIG. 8 illustrates a perspective view of a band type device for securing the accelerometer based device to the patient during data collection, according to an embodiment of the present invention. The device 200 includes a band 202 and a mount 204 for the accelerometer device 206. The band 202 can be formed from an elastic material, a soft and flexible fabric, or any other suitable material that would be comfortable to the patient during sleep. The band 202 can include a securement device 208 such as hook and loop closure, snaps, buttons, hook and eye, or any other suitable securement means known to or conceivable by one of skill in the art. The accelerometer device 206 can be held in a mount 204 in the form of a pouch, case, friction fit holder, or any other suitable mount known to or conceivable by one of skill in the art. The mount 204 can be configured to allow the patient to access and use any touch screen or buttons associated with the accelerometer device 206. It is also possible that the mount can be configured to accommodate devices of varying size, such that multiple band type devices do not need to be made for use with accelerometer devices with different shapes and sizes. The device may also be included in a wearable band that provides comfortable positioning of the device on the leg.

It should be noted that the computer application is programmed onto a non-transitory computer readable medium that can be read and executed by any of the computing devices mentioned in this application. The non-transitory computer readable medium can take any suitable form known to one of skill in the art. The non-transitory computer readable medium is understood to be any article of manufacture readable by a computer. Such non-transitory computer readable media includes, but is not limited to, magnetic media, such as floppy disk, flexible disk, hard disk, reel-to-reel tape, cartridge tape, cassette tapes or cards, optical media such as CD-ROM, DVD, Blu-ray, writable compact discs, magneto-optical media in disc, tape, or card form, and paper media such as punch cards or paper tape. Alternately, the program for executing the method and algorithms of the present invention can reside on a remote server or other networked device. Any databases associated with the present invention can be housed on a central computing device, server(s), in cloud storage, or any other suitable means known to or conceivable by one of skill in the art. All of the information associated with the application is transmitted either wired or wirelessly over a network, via the internet, cellular telephone network, or any other suitable data transmission means known to or conceivable by one of skill in the art.

The many features and advantages of the invention are apparent from the detailed specification, and thus, it is intended by the appended claims to cover all such features and advantages of the invention which fall within the true spirit and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

What is claimed is:

1. A method for tracking movements and positions of a leg or foot of a subject, comprising:
    launching, by a device, an application for monitoring and tracking the movements and positions of the leg or foot;
    activating, by the device and based on launching the application, a movement and position detector to collect data regarding the movements and positions of the leg or foot;
    collecting, by the device and based on activating the movement and position detector, the data regarding the movements and positions of the leg or foot,
        the data, regarding the movements and positions of the leg or foot, including information associated with a rotational movement;
    generating, by the device and based on collecting the data regarding the movements and positions of the leg or foot, a graphical output comprising an indication of one or more particular movements that satisfy a criteria for a movement from a lying down leg position,
        the criteria being satisfied based on a threshold activity, duration, and periodicity for time;
    providing, by the device, the graphical output; and
    transmitting, by the device, the data, regarding the movements and positions of the leg or foot, to a system cloud.

2. The method of claim 1, wherein collecting the data regarding the movements and positions of the leg or foot comprises:
    collecting the data regarding the movements and positions of the leg or foot for a predetermined period of time.

3. The method of claim 2, wherein generating the graphical output comprises:
    generating the graphical output over the predetermined period of time.

4. The method of claim 1, further comprising:
    prompting, based on launching the application, the subject to activate collection of the data regarding the movements and positions of the leg or foot.

5. The method of claim 1, further comprising:
    prompting, based on collecting the data regarding the movements and positions of the leg or foot, the subject to terminate the application.

6. The method of claim 1, wherein the movement and position detector is coupled with one of:
    a smartphone,
    a phablet,
    a tablet,
    a personal music device,
    a fitness tracker, or
    a leg band.

7. The method of claim 6, wherein the device is positioned in a mount on a strap configured to be secured to the leg or incorporated into a wearable strap.

8. The method of claim 1, further comprising:
    storing the data regarding the movements and positions of the leg or foot in a data structure.
9. The method of claim 1, wherein the movement and position detector comprises at least one of:
    an accelerometers, or
    a gyroscope.
10. A system for tracking movements and positions of a leg or foot of a subject, comprising:
    a memory; and
    one or more processors, communicatively coupled to the memory, to:
        launch an application for monitoring and tracking the movements and positions of the leg or foot;
        activate, based on launching the application, a movement and position detector configured to be placed on a leg of the subject and configured to collect data regarding the movements and positions of the leg or foot;
        collect, based on activating the movement and position detector, the data regarding the movements and positions of the leg or the foot,
            the data, regarding the movements and positions of the leg or foot, including information associated with a rotational movement;
        generate, based on collecting the data regarding the movements and positions of the leg or foot, a graphical output comprising an indication of one or more particular movements that satisfy a criteria for a movement from a lying down leg position,
            the criteria being satisfied based on a threshold activity, duration, and periodicity for time;
        provide the graphical output; and
        transmit the data, regarding the movements and positions of the leg or foot, to a system cloud.
11. The system of claim 10, wherein the one or more processors, when collecting the data regarding the movements and positions of the leg or foot, are to:
    collect the data, regarding the movements of the leg or foot, using at least one of an accelerometer or a gyroscope.
12. The system of claim 10, wherein the movement and position detector is coupled with one of:
    a smartphone,
    a phablet,
    a tablet,
    a personal music device,
    a fitness tracker, or
    a leg band.
13. The system of claim 10, where the application comprises a user interface for the subject to interact with the system.
14. The system of claim 10, further comprising:
    a wearable strap to hold the movement and position detector on the leg of the subject.
15. The method of claim 1, where generating the graphical output comprises:
    generating graphic and numeric outputs of sleep quality, position, and circadian rhythm.
16. The system of claim 10, wherein the one or more processors, when generating the graphical output, are to:
    generate the graphical output related to overall sleep quality, position, and circadian rhythm.

17. A non-transitory computer-readable medium storing instructions, the instructions comprising:
    one or more instructions that, when executed by one or more processors, cause the one or more processors to:
        launch an application for monitoring and tracking movements and positions of a leg or foot of a subject;
        activate, based on launching the application, a movement and position detector to collect data regarding the movements and positions of the leg or foot;
        collect, based on activating the movement and position detector, the data regarding the movements and positions of the leg or foot,
            the data, regarding the movements and positions of the leg or foot, including information associated with a rotational movement;
        generate, based on collecting the data regarding the movements and positions of the leg or foot, a graphical output comprising an indication of one or particular movements that satisfy criteria for a movement from a supine, prone, or lying-on-side leg position,
            the criteria being satisfied based on a threshold activity, duration, and periodicity for time;
        provide the graphical output; and
        transmit the data, regarding the movements and positions of the leg or foot, to a system cloud.
18. The non-transitory computer-readable medium of claim 17, wherein the one or more instructions, that cause the one or more processors to collect the data regarding the movements and positions of the leg or foot, cause the one or more processors to:
    collect the data, regarding the movements of the leg or foot, using at least one of an accelerometer or a gyroscope.
19. The non-transitory computer-readable medium of claim 17, wherein the one or more instructions, that cause the one or more processors to collect the data regarding the movements and positions of the leg or foot, cause the one or more processors to:
    collect the data, regarding the movements and positions of the leg or foot, for a predetermined period of time.
20. The non-transitory computer-readable medium of claim 19, wherein the one or more instructions, that cause the one or more processors to generate the graphical output, cause the one or more processors to:
    generate the graphical output over the predetermined period of time.
21. The non-transitory computer-readable medium of claim 17, wherein the one or more instructions, when executed by the one or more processors, cause the one or more processors to:
    prompt, based on launching the application, the subject to activate collection of the data regarding the movements and positions of the leg or foot.
22. The non-transitory computer-readable medium of claim 17, wherein the one or more instructions, when executed by the one or more processors, cause the one or more processors to:
    prompt, based on collecting the data regarding the movements and positions of the leg or foot, the subject to terminate the application.

* * * * *